(12) United States Patent
Zimmermann et al.

(10) Patent No.: US 8,993,308 B2
(45) Date of Patent: Mar. 31, 2015

(54) STORAGE DEVICE FOR CRYOPRESERVATION OF BIOLOGICAL SAMPLES

(75) Inventors: Heiko Zimmermann, St. Ingbert (DE); Günter R. Fuhr, Berlin (DE); Stephen Shirley, St. Ingbert (DE); Frank Ihmig, Sulzbach (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 1637 days.

(21) Appl. No.: 12/279,751
(22) PCT Filed: Jun. 15, 2007
(86) PCT No.: PCT/EP2007/005308
§ 371 (c)(1),
(2), (4) Date: Aug. 18, 2008
(87) PCT Pub. No.: WO2007/147531
PCT Pub. Date: Dec. 27, 2007

(65) Prior Publication Data
US 2009/0023128 A1 Jan. 22, 2009

(30) Foreign Application Priority Data
Jun. 20, 2006 (EP) .................................... 06012660

(51) Int. Cl.
*A01N 1/02* (2006.01)
*G01N 1/42* (2006.01)
*B01L 3/00* (2006.01)

(52) U.S. Cl.
CPC ................. *A01N 1/02* (2013.01); *B01L 3/5085* (2013.01); *B01L 3/545* (2013.01);
(Continued)

(58) Field of Classification Search
CPC ..... A01N 1/02; A01N 1/0268; A01N 1/0257; B02L 3/545; B02L 3/5085; B02L 2300/024; B02L 2300/023; G01N 1/42
USPC ........ 435/1.3; 340/585; 62/62, 171, 337, 441; 700/24, 202
See application file for complete search history.

(56) References Cited

U.S. PATENT DOCUMENTS 4,113,353 A * 9/1978 Matsushita ................... 359/636
6,931,864 B2 8/2005 Fuhr et al.
(Continued)

FOREIGN PATENT DOCUMENTS

DE 29912346 U1 12/1999
DE 10060889 A1 6/2002
(Continued)

OTHER PUBLICATIONS

International Search Report for PCT/EP2007/005308.
(Continued)

*Primary Examiner* — Michael Hobbs
(74) *Attorney, Agent, or Firm* — Caesar, Rivise, Bernstein, Cohen & Pokotilow, Ltd.

(57) ABSTRACT

A cryopreservation storage device (100), in particular for cryopreservation of biological samples, comprises a plurality of multi sample modules (20) being adapted for accommodating the biological samples and sample memories, a module control device (30) controlling an access to sample memories accommodated by the multi sample modules (20), and a data interface (41) for accessing to the module control device (30), wherein the module control device (30) includes a data management processor (31), which can be controlled via the data interface (41). Furthermore, a cryopreservation apparatus including at least one cryopreservation storage device (100) and a method for cryopreservation of biological samples are described.

17 Claims, 4 Drawing Sheets

(52) U.S. Cl.
CPC ..... *B01L 2300/023* (2013.01); *B01L 2300/024* (2013.01); *G01N 1/42* (2013.01); *A01N 1/0257* (2013.01); *A01N 1/0268* (2013.01)
USPC .................................................... 435/286.1

(56) References Cited

U.S. PATENT DOCUMENTS

| | | | | |
|---|---|---|---|---|
| 7,338,443 | B1* | 3/2008 | Tucker | 600/300 |
| 2001/0026778 | A1* | 10/2001 | Ackley et al. | 422/129 |
| 2005/0069861 | A1 | 3/2005 | Zimmermann et al. | |

FOREIGN PATENT DOCUMENTS

| | | |
|---|---|---|
| DE | 10202304 A1 | 7/2003 |
| EP | 0974798 B1 | 5/2004 |
| JP | 2004061427 A | 2/2004 |

OTHER PUBLICATIONS

Ihmig et al., "Cryogenic electronic memory infrastructure for physically related "continuity of care records" of frozen cells", Cryogenics, vol. 46 (2006), pp. 312-320.

* cited by examiner

STORAGE DEVICE FOR CRYOPRESERVATION OF BIOLOGICAL SAMPLES

SUBJECT OF THE INVENTION

The present invention relates to a cryopreservation storage device, in particular for cryopreservation of biological samples, in particular to a cryopreservation storage device for accommodating the biological samples and associated sample data. Furthermore, the present invention relates to a cryopreservation apparatus including a plurality of cryopreservation storage devices and to a method for cryopreservation of biological samples, in particular to method for processing sample data stored with biological samples in the cryopreservation storage device.

BACKGROUND ART

In the field of cryopreservation of biological samples, there is an increasing need for storing large numbers of samples at a cryopreservation temperature, like e.g. the temperature of liquid nitrogen or vapour of liquid nitrogen. The samples are stored in thermally insulated containers (so-called cryotanks).

Typically, the samples are deposited in combination with associated sample data including an identification of the samples and optionally further specific information, like e.g. properties of the sample's donor or data concerning a previous processing of the samples. In DE 100 60 889 A1, the combined arrangement of sample receptacles and sample memories in the cryo-tank has been proposed for ensuring that the correspondence of the sample and the assigned sample data is kept during the cryopreservation. The sample receptacles and memories are arranged on a common carrier or board, which includes a processor circuit for controlling the sample memories. All sample receptacles and memories are connected in parallel with the processor circuit.

For accessing to the sample data from outside the cryo-tank, a communication channel is required for connecting the sample memories with e.g. a host computer. If a plurality of sample receptacle and memory boards is arranged in the cryo-tank, particular demands are made on the communication channel as the processor circuits of the boards create a complex structure requiring a large number of wire-connections. The technique disclosed in DE 100 60 889 A1 has a restriction as it does not disclose an effective management of the data access to the plurality of sample receptacle and memory boards.

Wireless communication channels using transponder technology have been proposed in DE 102 02 304 A1 and DE 299 12 346 U1. The transponder technology has advantages in terms of avoiding any thermal bridge trough a wall of the cryo-tank. However, there are limitations if a large number of samples and sample data are to be handled. With increasing storing density, RFID transponders may interfere each other.

Another wireless communication channel for general applications has been developed with the WLAN technology, which, however, requires that all available clients are powered for an access from a host computer. Accordingly, the WLAN technology would have disadvantages if used for cryopreservation purposes as powered clients would provide heat sources in the cryo-tank.

Figure 6:
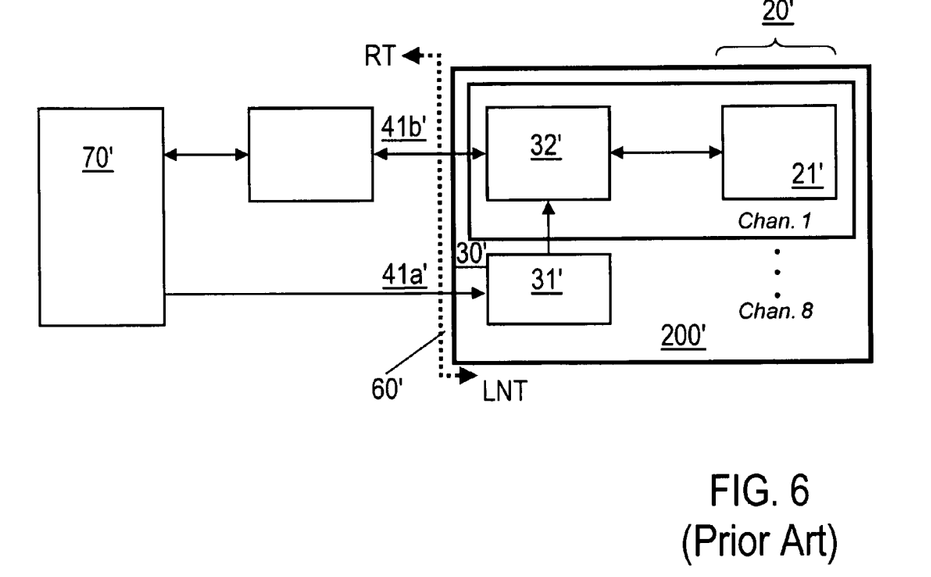
FIG. 6: a schematic illustration of aa conventional multiplexer system.

F. R. Ihmig et al. ("Cryogenics" vol. 46, 2006, p. 312 to 320) have proposed a wire-bound communication channel based on a multiplexer system as schematically illustrated in FIG. 6. The cryopreservation apparatus 200' comprises a multi sample module 20' including eight sample data memory cards 21' (FLASH memories), a module control device 30' for controlling an access to the memory cards accommodated by the multi sample module 20' and a host computer 70'. The components 20' and 30' are arranged in the cryo-tank 60' at cryopreservation temperature, while the host computer 70' is positioned at room temperature. The module control device 30' comprises an address logic 31' and an analog switch circuit 32'. The host computer 70' is connected via first and second data interfaces 41a', 41b' with the address logic 31' and the analog switch circuit 32', resp.

With an increasing number of samples and sample data, the conventional multiplexer system requires an increasing number of wire connections from the host computer 70' into the cryo-tank 60'. As an example, the conventional eight channel design requires 50 pin connections of the second data interfaces 41b'. In practice, even more, e.g. more than 200 wires would be necessary for connecting all sample data memory cards 21' with the host computer 70'. The increasing number of wire connections create a disadvantageous heat bridge having a negative effect on the temperature control of the cryo-tank. Another problem of the conventional multiplexer system is given by the fact that all sample data memory cards 21' have to be activated for accessing to any sample data. Activating all sample data memory cards 21' requires an essential power consumption and a corresponding generation of heat inside the cryo-tank. Accordingly, a further cooling efficiency of the conventional cryopreservation apparatus 200' can be limited. If the conventional multi sample module 20' is to be removed from the cryo-tank, another disadvantage arises due to the complex structure and large number of wire-connections of the multiplex system.

OBJECTIVE OF THE INVENTION

The present invention is based on the objective of providing an improved storage device for cryopreservation of biological samples avoiding the disadvantages of the conventional techniques. Furthermore, the present invention is based on the objective of providing an improved cryopreservation method.

SUMMARY OF THE INVENTION

The above objective is solved with a storage device, a cryopreservation apparatus or a cryopreservation method comprising the features of the invention.

According to a first aspect of the invention, the above objective is solved by the general technical teaching of providing a cryopreservation storage device (or briefly: storage device), which includes at least one multi sample module being capable of accommodating biological samples and sample memories, a module control device for serially accessing to all sample memories accommodated by the at least one or plurality of separate multi sample modules, and a data interface for accessing to the module control device, wherein the module control device includes a data management processor, which can be controlled via the data interface.

The multi sample module includes sample receptacles for depositing the biological samples. Furthermore, the multi sample module includes sample memories for storing data associated with the biological samples. The sample memories are fixedly positioned at the multi sample module. Alternatively, the multi sample module includes memory connectors for flexible connecting or separating the sample memories. Preferably, one sample receptacle is assigned to one sample memory, resp.

The module control device is a circuit with a plurality of circuit components controlling the access (reading/writing data) to all accessible sample memories accommodated by the multi sample module. The essential circuit component of the module control device is the data management processor, which fulfils the access control function in dependence on signals received via the data interface. Generally, the data management processor includes a micro controller being capable to run a software program and an associated processor memory. In particular, the data management processor is arranged for reading signals via the data interface, for addressing and accessing to sample memories accommodated by the multi sample module, and for transmitting sample data via the data interface. Additionally, the data management processor is arranged for controlling cryopreservation conditions, like e.g. the temperature of cryopreservation.

Preferably, the multi sample modules and the module control device are carried by a carrier board. The combination of the module control device and the multi sample modules represents a modular structure, which allows a simple adaptation to the requirements of a particular cryopreservation task. Furthermore, this combination represents a hierarchical structure, wherein the module control device is arranged for controlling a plurality of multi sample modules. Contrary to conventional techniques, the module control device being capable to take over functions of a host computer is arranged in the cryopreservation environment.

According to the invention, the operation of the data management processor is controlled via the data interface. In particular, the data management processor can be powered (switched on/switched off) by a control signal received by the storage device via the data interface. Preferably, the data interface is operated with a line-bound communication bus including in particular electrical wire and/or optical guide connections.

The provision of the data management processor and the operation thereof under cryopreservation conditions result in a series of the following advantages, which allow overcoming the above limitations of the conventional techniques.

Firstly, a large number of sample memories can be controlled with the data management processor via the single data interface. Due to a local data processing on the storage device, an increasing number of sample memories do not require an increasing number of wire connections. Accordingly a disadvantageous heat transfer via wire connections can be avoided.

Furthermore, due to the capability of controlling the data management processor operation via the single data interface on demand, power consumption and corresponding heat generation inside a cryo-tank can be reduced by switching the data management processor of a particular storage device for certain operation requests only. If a plurality of storage devices are commonly arranged in the cryo-tank, only a single data management processor of a particular storage device can be powered, while the data management processor of the remaining storage devices can be kept switched-off.

Furthermore, the data management processor structure allows providing the sample memories with an essentially simplified design. According to the invention, each of the sample memories comprises a memory circuit chip without an additional memory controller. Low-cost single memory circuit chips, like e.g. available FLASH memories can be used, so that an essential advantage is obtained even with increasing numbers of samples an sample data to be stored.

Furthermore, the data management processor allows implementing new functions in terms of sample data processing, like monitoring, evaluating and self-documenting of sample data. These functions can be fulfilled by the software program running on the data management processor independently on an additional communication with any host computer.

The data management processor has a further essential advantage in terms of security of cryopreservation. Data from a host computer can be mirrored in the processor memory of the data management processor. Furthermore, the storage device including the data management processor represents a self-sufficient unit, which can be transferred without lost of data from a cryo-tank to another location, like e.g. another cryo-tank.

According to a second independent aspect of the invention, the above objective is solved by the general technical teaching of providing a cryopreservation apparatus comprising at least one storage device according to the above first aspect of the invention, which at least one storage device being arranged in a cryo-storage container for the cryopreservation of the biological samples. Generally, the cryo-storage container (also: cryo-tank) is a container being capable of accommodating the at least one storage device and cooling media and having a thermally insulated wall.

The cryopreservation apparatus of the invention has an essential advantage in that all storage devices being commonly arranged in the cryo-storage container can be controlled via one single data interface. The data interface is commonly shared by all storage devices. Accordingly, the storage devices can be connected with a host computer outside the cryo-storage container via a low number (e.g. <10) of connection lines, even if more than ten storage devices each comprising more than 500 memory circuit chips are arranged in the cryo-storage container.

According to a third independent aspect of the invention, the above objective is solved by the general technical teaching of providing a method for cryopreservation of biological samples, wherein the biological samples and associated sample data are arranged in at least one storage device according to the above first aspect of the invention at a predetermined cryopreservation temperature and wherein a data interface is used for controlling the data management processor of the module control device as well as for accessing to the sample data.

According to a preferred embodiment of the invention, the data management processor is connected with a power control device included in the storage device. Advantageously, the data management processor can be powered with the power control device in response to a power signal (storage device address signal) received via the data interface.

According to a particularly preferred embodiment of the invention, the storage device has a completely serial design. All data communication is provided via serial lines (buses). In particular, the data interface is a serial data interface for a serial communication from a host computer with the data management processor. With the cryopreservation method of the invention, signals for controlling the data management processor of the module control device and for accessing to the sample data are serially transferred.

According to a further preferred embodiment of the invention, a base unit is provided including the data interface and the power control device of the storage device. The base unit comprises a circuit board carrying the data interface and the power control device, while the multi sample units and the module control device are arranged on at least one separate board, in particular on a common rack. The base unit has a particular advantage for handling the storage device of the invention with practical cryopreservation conditions. As an example, the base unit (or a plurality of base units) can be fixedly arranged in the cryo-storage container for flexible coupling the common rack with the multi sample units and the module control device. Accordingly, a preferred embodiment of the invention is characterized by a separable connection between the base unit and the multi sample modules and/or the module control device. With the method of the invention, the multi sample modules and the module control device can be commonly separated from the base unit. Particularly preferred is the provision of an optical communication channel between the base unit and the module control device, so that the separation of the multi sample units and the module control device from a particular base unit is facilitated. The base unit can be arranged below of or above the multi sample modules and/or the module control device.

According to the invention, the module control device is adapted for a serial access to the sample memories on the multi sample modules. Preferably, each multi sample module is adapted for accommodating at least 50 samples and 50 sample memories, e.g. 256 samples and 256 sample memories or more. According to a particular preferred embodiment of the invention, each multi sample module comprises a matrix board for accommodating the biological samples and the sample memories. The matrix board can be fixed to the common rack (carrier board) additionally carrying the module control device. Alternatively, the matrix board can be set via a plug contact on the common rack. The matrix board comprises a matrix arrangement of the biological samples and sample data memories e.g. with straight rows and columns. As essential advantages, the access to and addressing of the data is facilitated and the structural complexity is reduced. In particular, the matrix board facilitates the serial access to the sample memories.

Preferably, the multi sample module (matrix board) comprises a matrix arrangement of the biological samples and sample memories, a row address selector and a column address selector being adapted for accessing to one of the sample memories. With this embodiment, memory access is essentially simplified by selecting one of the sample memories by a row signal (clock signal) and a column signal (chip select signal) supplied via the row address selector and the column address selector, resp. Preferably, the data management processor and in particular the data interface is adapted for supplying the row and column signals. The matrix arrangement allows the provision of a minimum of connection lines and circuitry. Thus, an advantage is obtained in particular with regard to the operation in cryopreservation conditions.

According to a further particularly preferred embodiment of the invention, the data management processor is adapted for a specific activation of a single one of the matrix boards. Again, an essential reduction of power consumption can be obtained in the cryo-storage container.

Another advantage of the invention is given by high flexibility in terms of using different types of data interfaces, in particular serial data interfaces. According to a preferred embodiment of the invention, the data interface is a Serial Peripheral Interface (in the following: SPI interface).

The SPI interface comprises a synchronized serial data bus with only three connection input lines. Advantageously, all data communications between the host computer and the at least one storage device can be implemented via these three connection lines, to which all storage devices are connected in parallel. A further advantage of the SPI interface is the high clock frequency, which can be used up to the MHz-range. Alternatively, the data interface can comprise the so-called "Microwire"-bus system (National Semiconductor).

According to a further advantageous embodiment of the invention, all components of the cryopreservation storage device are capable to be operated at a predetermined cryopreservation temperature, in particular at the temperature of liquid nitrogen or vapour of liquid nitrogen. Preferably, the cryopreservation temperature is set with the cryo-storage container of the cryopreservation storage device of the invention.

If according to a further advantageous modification of the invention, the storage device comprises an opto-electrical converter being connected with the data interface, the data communication with the host computer can be improved. Preferably, the opto-electrical converter is adapted for an operation at the cryopreservation temperature as well. Accordingly, data can be optically transferred via optical wires through a wall of the cryo-storage container.

According to a further preferred embodiment, the cryopreservation apparatus of the invention comprises a host computer, which is located outside the cryo-storage container. Preferably, the storage devices are connected with the host computer via the serial SPI bus.

BRIEF DESCRIPTION OF THE DRAWINGS

Further details and advantages of the invention are described in the following with reference to the attached drawings, which show in.

PREFERRED EMBODIMENTS OF THE INVENTION

The preferred embodiments of the invention are described in the following with reference to schematic drawings and diagrams of the circuit components used for providing the cryopreservation storage device and the cryopreservation apparatus, respectively. It is emphasised that the scope of the claims is not restricted to the illustrated embodiments. In particular, the number of multi sample modules and storage devices, the design of the multi sample modules, the shape of the cryo-tank, the functions for operating and controlling the cryopreservation apparatus and the connection with one or more host computers can be varied by the skilled person in dependence on the requirements of a particular cryopreservation task and application.

Figure 1:
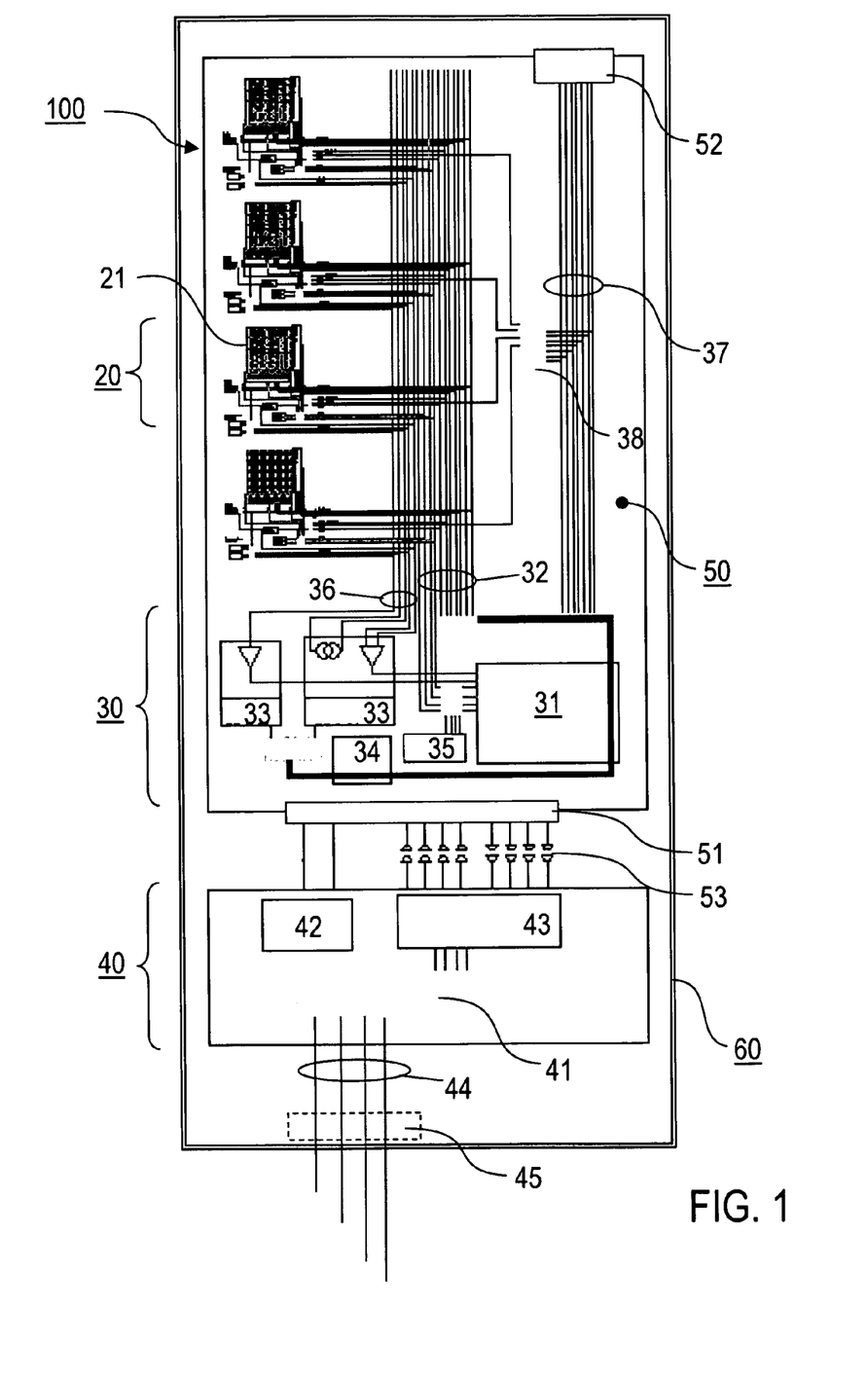
FIG. 1: a preferred embodiment of a storage device in accordance with the present invention.

According to FIG. 1, the cryopreservation storage device 100 comprises a plurality of multi sample modules 20, the module control device 30, the base unit 40 and optionally an opto-electrical converter 45. For cryopreservation purposes, these components are arranged in a cryo-tank 60.

Each of the multi sample modules 20 comprises a matrix board 21 including a matrix arrangement of sample memories 10 (see FIG. 5) and further board circuits, which are described below with reference to FIGS. 4 and 5. All of the multi sample modules 20 are connected with one single module control device 30.

The module control device 30 comprises the data management processor 31, a module control bus 32 for accessing to the multi sample modules 20, power control circuits 33 for activating single sample memories, matrix boards or further circuit components of the multi sample modules 20, and further memories, like RAM 34 and FLASH memory 35 for storing further specific information concerning control and operations of the module control device 30. The data management processor 31 comprises a microcontroller fur running a module control software program and a processor memory for storing data used by the module control software program.

The base unit 40 comprises the SPI interface 41, the power control device 42 and a communication switching circuit 43. The SPI interface 41 can be connected via the SPI bus 44 and optionally the opto-electrical converter 45 with a host computer 70 (see FIG. 2). Further details of the SPI interface 41 are described below with reference to FIG. 3.

The multi sample modules 20 and the module control device 30 are arranged on a common carrier board 50. In practise, the carrier board 50 is vertically directed, so that the multi sample modules 20 are arranged like a stack above the module control device 30. Accordingly, the carrier board is also called tower 50.

The carrier board 50 carries not only the circuit parts of the component 20 and 30, but also connectors 51, 52, which are provided on a lower and an upper end of the carrier board 50, respectively. The first connector 51 on the lower end of the carrier board 50 provides the communication channel with the base unit 40. Preferably, at least the connections with the communications switching circuit 43 are implemented with opto-couplers 53, so that connecting or disconnecting of the carrier board 50 relative to the base unit 40 is facilitated. The second connector 52 at the upper end of the carrier board 50 is optionally provided for an additional access to the components 20 and/or 30. After removing the carrier board 50 from the cryo-tank 60, the whole tower can be set e.g. on a laboratory table. In this situation, the second connector 52 at the upper end of the carrier board 50 can be advantageously used instead of the first connector 51.

Furthermore, the carrier board includes wired connections, like e.g. the module control bus 32, the power lines 36 for activating the multi sample modules 20 and an address bus 37 for addressing one or more multi sample modules 20 using the address switch 38.

The cryopreservation storage device 100 according to FIG. 1 can be adapted for accommodating 256 samples on each of the matrix boards 21, while 64 slots for accommodating matrix boards 21 can be provided on the carrier board 50. Accordingly, 16.384 sample memories can be managed by the data management processor 31, which can be completely controlled via the SPI bus 44. This represents an essential advantage compared with the conventional multiplexer technique, which correspondingly would require about 400 wire connections for controlling a comparable number of samples.

Figure 2:
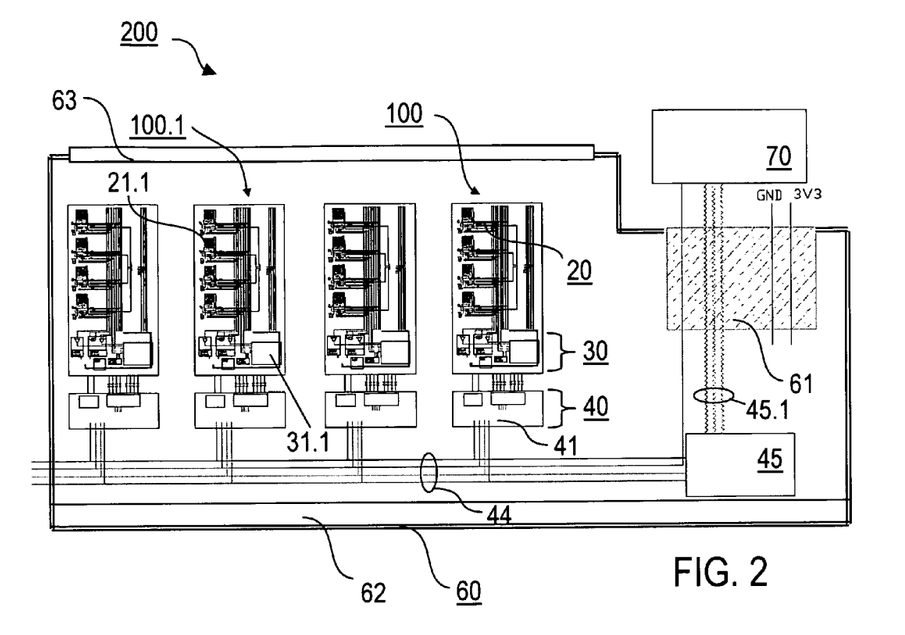
FIG. 2: a preferred embodiment of a cryostorage apparatus in accordance with the present invention.

FIG. 2 illustrates a preferred embodiment of the cryopreservation apparatus 200 comprising a plurality of cryopreservation storage devices 100, which are arranged in the cryo-tank 60 and connected with the host computer 70. The host computer 70 includes a computer unit as well as a power supply, a power monitor, signal converter and signal driver for controlling the cryopreservation storage devices 100 in the cryo-tank 60. Each of the cryopreservation storage devices 100, in particular with the components 20 to 50 is structured as described above with reference to FIG. 1. All cryopreservation storage devices 100 are connected via a common SPI bus 44 and the opto-electrical converter 45 with the host computer 70. The wire and/or optical guide connections 45.1 from the opto-electrical converter 45 to the host computer 70 run through the cryo-tank insulation 61, which is partially shown with an enlarged view.

The cryo-tank 60 is structured as it is known from conventionally available cryo-tanks. In particular, the cryo-tank 60 includes a cooling medium 62, like liquid nitrogen and vapour of the liquid nitrogen, and a cover lid 63.

Figure 3:
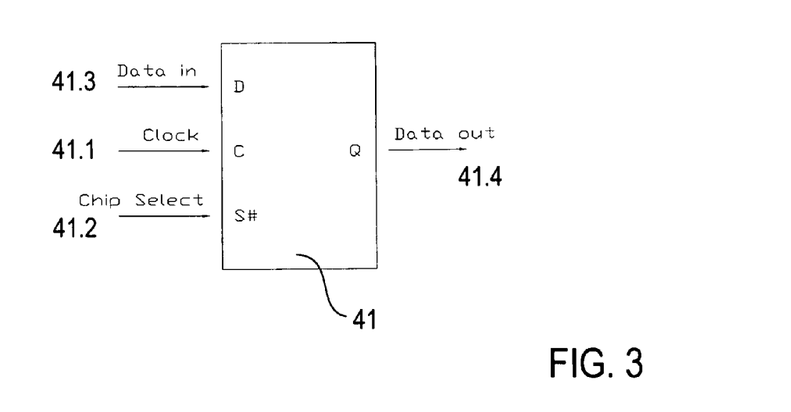
FIG. 3: a schematic illustration of an SPI interface used in accordance with the present invention.

FIG. 3 schematically illustrates the SPI interface 41, which is provided according to the generally known industry standard. The SPI interface 41 comprises four signal lines only, namely a serial clock line 41.1, a chip select line 41.2, a data in line 41.3 and a data out line 41.4. All cryopreservation storage devices 100 can be connected with the SPI interface 41 in parallel. Via the SPI interface 41, a column signal (chip select signal) and a row signal (clock signal) are supplied to the row and column address selectors 22, 23 of the multi sample module 20 (see below).

Figure 4:
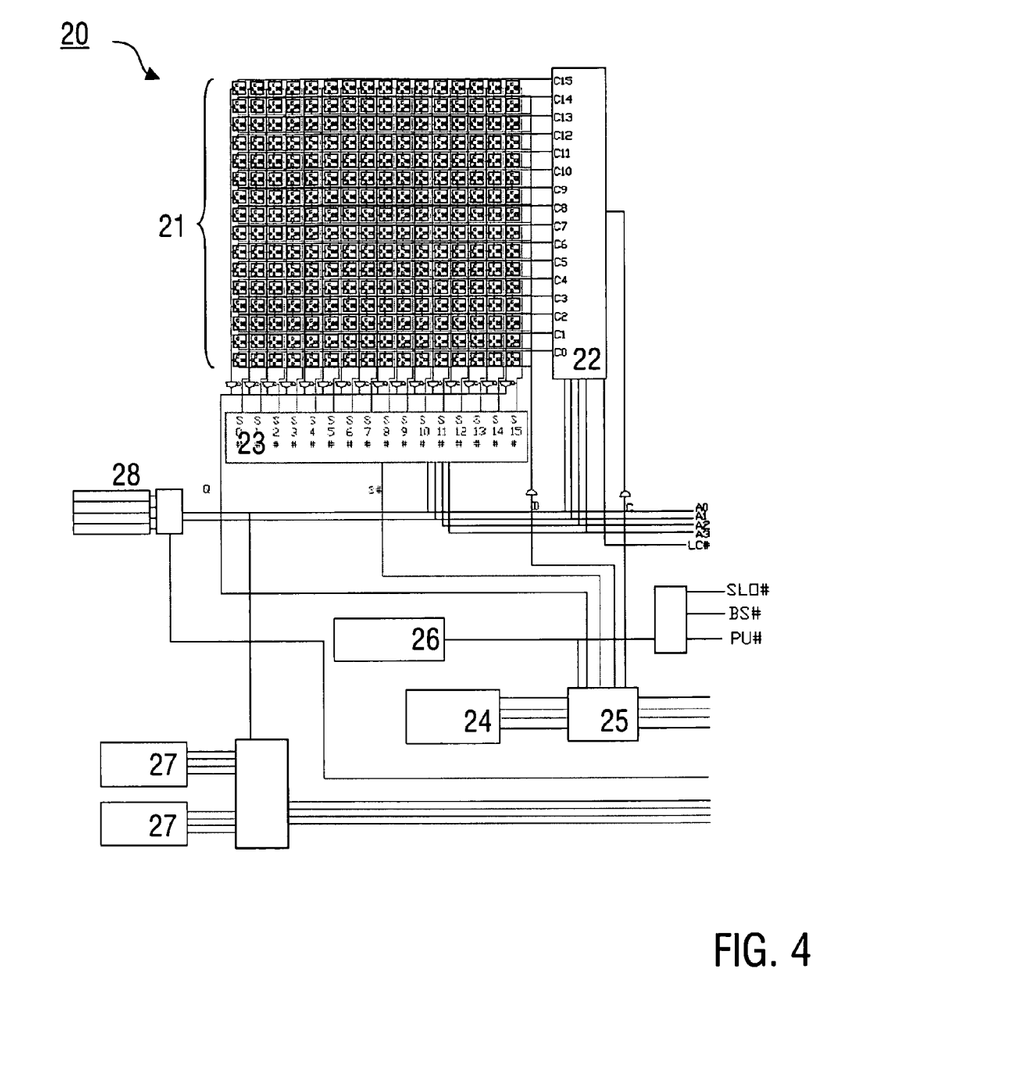
FIG. 4: a schematic illustration of a multi sample module including a matrix board.
Figure 5:
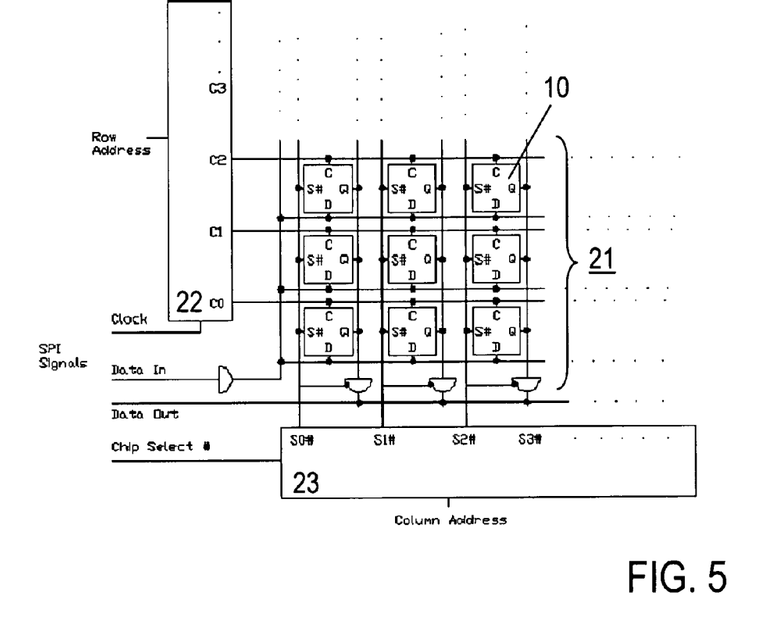
FIG. 5: further details of the matrix board according to FIG. 4.

FIGS. 4 and 5 illustrate further details of the multi sample module 20 including the matrix board 21 with a row address selector 22 and a column address selector 23 as well as further board circuits 24 to 27. All of these components are arranged on a common board which can be set in a corresponding slot on the carrier board (tower) 50. The board circuits comprise a board memory chip 24, a switching circuit 25, a power control 26, temperature sensors 27 and light-emitting diodes (LED's) 28. The board memory chip 24 is adapted for storing information related to the matrix board 21 as such, like information on the board type and board geometry.

The temperature sensors 27 are adapted for sensing the temperature at different positions of the matrix board 21. The temperature sensors comprise e.g. a PT100 sensor. The LED's 28 are adapted for indicating an operation condition of the matrix board 21, like e.g. an interaction of one of the sample memories 10 with the module control device 30 (see FIG. 1) and/or the host computer 70 (see FIG. 2).

The method for cryopreservation according to the invention comprises the following procedural steps. Firstly, the biological samples and associated sample data are stored in at least one of the multi sample modules of the cryopreservation storage device at the cryopreservation temperature. For this purpose, the following preparation steps can be implemented.

Depending in particular on the number of biological samples and the cryopreservation task, an appropriate design of the carrier board (tower) 50 can be selected. As an example, the sample receptacles included in the multi sample module 20 may comprise larger compartments for accommodating e.g. cell groups or tissue compared with smaller compartments for accommodating e.g. single biological cells. Accordingly, the design of the carrier board 50 can be selected to receive a small number (e.g. 10) of multi sample modules 20 for larger biological samples, or a larger number of multi sample modules (e.g. 100) for accommodating smaller biological samples. The same concept can be applied with regard to the sample data associated to the biological samples.

This capability of charging the carrier board 50 with different types or sizes of multi sample modules while the format of the connection with the base unit 40 is kept constant represents an essential advantage to the invention in terms of flexibility of using a cryo-tank 60.

The preparation of the cryopreservation storage device further may comprise storing of a particular module control software program in the data management processor 31 or particular information in the FLASH memory 35 (FIG. 1) and/or the board memory 24 (FIG. 4). As an example, the FLASH memory includes data on the type and properties of the tower 50, while the board memory 24 includes data on the type and properties of the matrix board 21. Both groups of data facilitate the recognition of the particular cryopreservation storage device 100 and the particular matrix board 21 by the host computer 70.

As a further procedural step of the cryopreservation method of the invention, the multi sample modules 20 are controlled by the module control device 30 in particular by the data management processor 31 of the corresponding cryopreservation storage device 100. For this purpose, the common SPI bus 44 is used both for controlling the data management processor(s) 31 and for accessing to the sample data.

As an example, if sample data are to be read on matrix board 21.1 of the cryopreservation storage device 100.1 (FIG. 2), the data management processor 31.1 of this particular device 100.1 is switched on. For this purpose, a power signal is transmitted via the SPI bus 44 to all SPI interfaces 41 of the cryopreservation storage devices included in the cryo-tank 60. The power signal includes the address of the particular device 100.1 so that only the data management processor 31.1 thereof is switched on while the other processors are kept in the non-activated condition. The power signal is transmitted via the line 41.2 of the SPI data interface 41. Correspondingly, the power consumption in the cryo-tank 60 is minimized.

Subsequently, a chip select message is transmitted via the SPI interface 41 to the data management processor 31.1. The data management processor 31.1 includes a complete directory of the sample memories accommodated in the associated multi sample modules on the particular cryopreservation storage device 100.1. Accordingly, the data management processor 31.1 can activate the appropriate matrix board 21.1 for reading or writing sample data in a particular sample memory.

Subsequently, a command signal can be transmitted via the SPI interface 41. As an example, the command signal may comprise the command "COMPILE AN INVENTURE" or "IDENTIFY EMPTY SPACE". According to the particular command signal, data from the matrix board 21.1 are processed as requested.

Accordingly, at least one of the following functions can be fulfilled by the SPI interface 41. Firstly, the particular tower 50 of one of the cryopreservation storage devices 100 can be switched on or switched off. Secondly, chip select signals can be routed to the tower 50 for accessing to a particular matrix board. Thirdly, command signals can be routed to the data management processor of the particular tower 50.

The invention has the following further advantages. By providing the data management processor on each tower, the number of connections to the outside host computer can be essentially reduced. Particularly, only 8 optical line-bound and 2 wire-bounded power connections are necessary for routing the SPI signals and further data, like e.g. sensor signals. Each tower arranged in the cryo-tank 60 is automatically connected with the base unit 40 and correspondingly with the SPI bus 44. On the other hand, the tower can be simply removed (lifted) by pulling out the carrier board 50. Each data management processor has an exclusively serial link to the base unit and the host computer. The group of data management processors of different cryopreservation storage devices advantageously represent a delocalised directory of sample data and memory information, which facilitates the automatic access to the sample data.

The features of the invention disclosed in the preceding description, the drawings and the claims can be important both singly and in combination for the implementation of the invention in its various aspects and embodiments.

The invention claimed is:

1. Cryopreservation storage device for cryopreservation of biological samples, comprising:
   a plurality of multi sample modules, each module including a plurality of sample receptacles in a matrix arrangement and a plurality of sample memories, each sample receptacle having a sample memory and being configured for depositing a biological sample, the plurality of sample memories configured for storing data associated with the biological samples, each one of the sample receptacles being assigned to a respective sample memory;
   a module control device configured to serially access all the sample memories accommodated by the multi sample modules and including a data management processor;
   a power control device configured to power the data management processor in response to a power signal; and
   a data interface for accessing the module control device, wherein the data management processor is configured to be controlled via the data interface, the data management processor being configured to read signals via the data interface, for serial access to the sample memories, and for transmitting sample data via the data interface, wherein the data interface is a serial interface configured for a serial communication from a host computer with the data management processor, and wherein
   the power control device is configured to receive the power signal via the data interface.

2. The cryopreservation storage device according to claim 1, wherein the data interface provides a serial access to the data management processor.

3. The cryopreservation storage device according to claim 1, further comprising a base unit, wherein the data interface and the power control device are arranged at the base unit.

4. The cryopreservation storage device according to claim 3, wherein the multi sample modules and the module control device are separable from the base unit.

5. The cryopreservation storage device according to claim 3, wherein the base unit and the module control device are optically coupled.

6. The cryopreservation storage device according to claim 1, wherein
   each of the multi sample modules comprises a matrix board for accommodating the biological samples and the sample memories, and
   the data management processor is adapted for a specific activation of one of the matrix boards.

7. The cryopreservation storage device according to claim 6, wherein the matrix board comprises a matrix arrangement of the biological samples and sample memories, a row address selector and a column address selector being adapted for accessing one of the sample memories.

8. The cryopreservation storage device according to claim 1, wherein the data interface is an SPI interface.

9. The cryopreservation storage device according to claim 1, wherein the multi sample modules, the module control device and the data interface are adapted for an operation at a predetermined cryopreservation temperature of the temperature of liquid nitrogen or vapour of liquid nitrogen.

10. The cryopreservation storage device according to claim 1, further comprising an opto-electrical converter being connected with the data interface.

11. The cryopreservation storage device according to claim 10, wherein the opto-electrical converter is adapted for an operation at a predetermined cryopreservation temperature of the temperature of liquid nitrogen or vapour of liquid nitrogen.

12. The cryopreservation storage device according to claim 1, wherein the data interface is connected with a line-bound communication bus.

13. The cryopreservation storage device according to claim 1, wherein the multi sample modules and the module control device are arranged on a common carrier board.

14. The cryopreservation apparatus, comprising:
   at least one cryopreservation storage device according to claim 1, and
   a storage container being adapted for cryopreservation of a plurality of biological samples, wherein the at least one storage device is arranged in the storage container.

15. The cryopreservation apparatus according to claim 14, comprising a plurality of cryopreservation storage devices, which share a common serial bus.

16. The cryopreservation apparatus according to claim 15, further comprising a host computer, wherein the at least one cryopreservation storage device is connected via the serial bus with the host computer.

17. The cryopreservation storage device according to claim 1, wherein the data management processor is configured to read signals via the data interface, for serial access to the sample memories, and for transmitting sample data via the data interface via execution of program steps by the data management processor.

* * * * *